(12) United States Patent
Daye (10) Patent No.: US 12,295,629 B2
(45) Date of Patent: May 13, 2025

(54) TIBIAL PLATEAU LEVELING OSTEOTOMY PLATE WITH OFFSET

(71) Applicant: Movora, LLC, Boston, MA (US)

(72) Inventor: Robert Mark Daye, Medina, OH (US)

(73) Assignee: Movora, LLC, Boston, MA (US)

( * ) Notice: Subject to any disclaimer, the term of this patent is extended or adjusted under 35 U.S.C. 154(b) by 0 days.

(21) Appl. No.: 17/026,931

(22) Filed: Sep. 21, 2020

(65) Prior Publication Data

US 2021/0085380 A1  Mar. 25, 2021
US 2021/0298806 A2  Sep. 30, 2021

Related U.S. Application Data

(60) Provisional application No. 62/903,110, filed on Sep. 20, 2019.

(51) Int. Cl.
| | |
|---|---|
| *A61B 17/80* | (2006.01) |
| *A61B 17/00* | (2006.01) |
| *A61B 17/15* | (2006.01) |
| *A61B 17/70* | (2006.01) |

(52) U.S. Cl.
CPC .............. *A61B 17/8061* (2013.01); *A61B 2017/00738* (2013.01); *A61B 17/157* (2013.01); *A61B 17/7059* (2013.01); *A61B 17/8014* (2013.01); *A61B 17/8052* (2013.01); *A61B 17/8057* (2013.01)

(58) Field of Classification Search
CPC .............. A61B 17/8061; A61B 17/157; A61B 17/7059; A61B 17/80; A61B 17/8052; A61B 17/8057; A61B 17/808; A61B 17/8095
USPC ............... 606/280, 286, 88, 87, 902, 86 B
See application file for complete search history.

(56) References Cited

U.S. PATENT DOCUMENTS

| | | | |
|---|---|---|---|
| 5,053,039 A | * | 10/1991 | Hofmann ............... A61B 17/15 606/87 |
| 6,183,475 B1 | * | 2/2001 | Lester ............... A61B 17/8095 606/281 |
| D536,453 S | | 2/2007 | Young et al. |
| 7,722,653 B2 | | 5/2010 | Young et al. |
| 7,740,648 B2 | | 6/2010 | Young et al. |
| 7,905,883 B2 | | 3/2011 | Bruecker et al. |
| 8,080,010 B2 | | 12/2011 | Schulz et al. |
| 8,118,846 B2 | | 2/2012 | Leither et al. |

(Continued)

FOREIGN PATENT DOCUMENTS

| | | |
|---|---|---|
| CN | 106037914 A | 10/2016 |
| CN | 107928774 A | 4/2018 |
| EP | 3023068 A2 | 5/2016 |

OTHER PUBLICATIONS

International Search Report of the International Searching Authority mailed on Dec. 2, 2020, issued in connection with International Application No. PCT/US2020/51769 (3 pages).

(Continued)

*Primary Examiner* — Marcela I. Shirsat
(74) *Attorney, Agent, or Firm* — Klarquist Sparkman, LLP (57) ABSTRACT

The device is a tibial plateau leveling osteotomy (TPLO) plate is used to stabilize a stifle joint in an animal in veterinary surgery after a torn cranial cruciate ligament. The TPLO plate has a proximal portion and a distal portion, connected by an offset portion. The proximal portion and at least a portion of the distal portion are formed on two parallel planes.

21 Claims, 6 Drawing Sheets

(56) References Cited

U.S. PATENT DOCUMENTS

| | | | |
|---|---|---|---|
| 8,317,842 | B2 | 11/2012 | Graham et al. |
| 8,523,921 | B2 | 9/2013 | Horan et al. |
| 9,204,912 | B2 | 12/2015 | Price et al. |
| D765,844 | S | 9/2016 | Dacosta |
| D766,434 | S | 9/2016 | DaCosta |
| D767,136 | S | 9/2016 | Paik |
| D780,922 | S | 3/2017 | Dacosta |
| D780,923 | S | 3/2017 | DaCosta |
| D780,925 | S | 3/2017 | DaCosta |
| D785,178 | S | 4/2017 | Kohler et al. |
| D787,060 | S | 5/2017 | Kohler et al. |
| D812,757 | S | 3/2018 | Barmes et al. |
| 10,245,088 | B2 | 4/2019 | Dayton et al. |
| 10,299,841 | B2 | 5/2019 | Dunlop et al. |
| D874,003 | S | 1/2020 | DaCosta et al. |
| D874,004 | S | 1/2020 | DaCosta et al. |
| D874,650 | S | 2/2020 | Horan et al. |
| 10,786,290 | B2 | 9/2020 | Horan et al. |
| 10,905,479 | B2 | 2/2021 | Horan et al. |
| 11,026,728 | B2 | 6/2021 | Horan et al. |
| D945,623 | S | 3/2022 | Daye |
| D977,645 | S | 2/2023 | Mason et al. |
| D977,646 | S | 2/2023 | Mason et al. |
| D1,018,854 | S | 3/2024 | Daye |
| 2006/0089648 | A1* | 4/2006 | Masini ............... A61B 17/1615 606/291 |
| 2006/0149275 | A1 | 7/2006 | Cadmus |
| 2007/0233106 | A1 | 10/2007 | Horan et al. |
| 2008/0039851 | A1 | 2/2008 | Schulz et al. |
| 2009/0024172 | A1* | 1/2009 | Pizzicara ........... A61B 17/8014 606/280 |
| 2010/0030276 | A1* | 2/2010 | Huebner ............ A61B 17/8061 606/280 |
| 2012/0265254 | A1 | 10/2012 | Horan et al. |
| 2013/0338781 | A1 | 12/2013 | Bordeaux et al. |
| 2014/0180343 | A1* | 6/2014 | Gaudin ................ A61F 2/4225 606/283 |
| 2016/0128745 | A1* | 5/2016 | Sidebotham ....... A61B 17/8014 606/281 |
| 2016/0135858 | A1* | 5/2016 | Dacosta ............. A61B 17/1728 606/280 |
| 2016/0310184 | A1 | 10/2016 | Kazanovicz et al. |
| 2017/0007304 | A1* | 1/2017 | Kuroda .............. A61B 17/8061 |
| 2018/0325568 | A1 | 11/2018 | Wotton |
| 2019/0069937 | A1 | 3/2019 | Kuroda et al. |
| 2019/0274743 | A1 | 9/2019 | Dunlop et al. |
| 2021/0212738 | A1 | 7/2021 | Daye |
| 2021/0361331 | A1 | 11/2021 | Daye |

OTHER PUBLICATIONS

Written Opinion of the International Searching Authority mailed on Dec. 2, 2020, issued in connection with International Application No. PCT/US2020/51769 (5 pages).

Notice of Allowance dated Nov. 2, 2021, issued in connection with U.S. Appl. No. 29/771,085 (7 pages).

International Preliminary Report on Patentability of the International Searching Authority mailed on Feb. 17, 2022, issued in connection with International Application No. PCT/US2020/51769 (14 pages).

Notice of Allowance dated Sep. 14, 2021, issued in connection with U.S. Appl. No. 29/771,085 (6 pages).

International Search Report of the International Searching Authority mailed on Jun. 16, 2022, issued in connection with International Application No. PCT/US2022/22012 (3 pages).

Written Opinion of the International Searching Authority mailed on Jun. 16, 2022, issued in connection with International Application No. PCT/US2022/22012 (8 pages).

Declaration of Alex Khowaylo dated Oct. 20, 2022, attaching image of Cloverleaf Plate with Parallel Screws, a product that was availble prior to Sep. 20, 2019 (2 pages).

Office Action mailed Sep. 1, 2023, issued in connection with U.S. Appl. No. 17/213,114 (13 pages).

Extended European Search Report dated Sep. 26, 2023, issued by the European Patent Office in connection with European Patent Application No. 20866115.7 (11 pages).

Office Action mailed Oct. 10, 2023, issued in connection with U.S. Appl. No. 17/393,616 (17 pages).

Notice of Allowance mailed Oct. 16, 2023, issued in connection with U.S. Appl. No. 29/829,907 (7 pages).

Office Action dated Nov. 20, 2023, issued by the Canadian Patent Office in connection with Canadian Patent Application No. 3, 155, 188 (4 pages).

Office Action issued in U.S. Appl. No. 17/213,114 on Mar. 27, 2024 (9 pages).

Office Action issued in U.S. Appl. No. 17/393,616 on Jun. 11, 2024 (12 pages).

Office Action issued in U.S. Appl. No. 17/213,114 on Jun. 26, 2024 (12 pages).

Extended European Search Report dated Mar. 24, 2025, issued by the European Patent Office in connection with European Patent Application No. 22776751.4 (13 pages).

\* cited by examiner

TIBIAL PLATEAU LEVELING OSTEOTOMY PLATE WITH OFFSET

CROSS-REFERENCE TO RELATED APPLICATIONS

This application claims the priority of U.S. Provisional Application Ser. No. 62/903,110, filed on Sep. 20, 2019, the contents of which are hereby incorporated by reference in its entirety and for all purposes.

BACKGROUND

Technical Field

The present disclosure relates to a tibial plateau leveling osteotomy plate (TPLO) with an offset, typically for use in veterinary surgery, with an animal, such as, but not limited to, a canine, a feline, or other quadruped animal species, both domestic and exotic.

Related Art

A tibial plateau leveling osteotomy (TPLO) plate is used in veterinary surgery to stabilize a stifle joint in an animal after a torn cranial cruciate ligament.

Current TPLO plates, when applied at an angle in a plane deviating from parallel to the long axis of the tibia, often result in abnormal angulation of the plate and screws, with the ensuing risk that a fixed angle screw could engage or enter structures such as joints, bones, or soft-tissue. Where the tibial plateau is translated during TPLO and the plate becomes offset from the bone surface, there can be increased bending stress placed on the screws, leading to cyclical loading to failure at far fewer cycles. Variations of anatomy, such as a mediolateral flared "trumpet-like" proximal tibia, can also lead to similar issues of plate offset from bone surface and angulation, even if the tibial plateau is rotated (leveled) without intentionally or unintentionally inducing translation in the mediolateral plane. Due to this unusual anatomy, an out-of-parallel plate application can result using the standard angle-stable TPLO plate.

SUMMARY

The present disclosure relates to a tibial plateau leveling osteotomy (TPLO) plate with offset. The TPLO plate with offset includes distal portion, an offset portion, and a proximal portion. The distal portion includes attachment apertures to secure the TPLO plate with offset to the body of the tibia. The proximal portion includes attachment apertures to secure the TPLO plate to an upper portion of a tibia or the osteotomized section of a tibia. The offset portion connects the proximal portion and the distal portion in an offset relation. The offset portion, or step or jog can be at 90° (i.e., perpendicular) or less than 90° with respect to both the distal portion and the proximal portion, such that the distal portion and the proximal portion are in parallel planes offset from each other. However, a section of the proximal portion may be twisted, rotated or inclined with respect to the plane of the remaining section of the proximal portion.

The TPLO plate typically allows mediolateral translation of the tibial plateau segment during TPLO and further typically allows the concurrent treatment of cranial cruciate ligament rupture and medial patella luxation. The TPLO plate is typically adapted to patients with trumpet-shaped or markedly flared proximal tibial anatomy or to patients with profound medial buttress (without necessitating extensive buttress elevation). The TPLO plate further is typically designed to facilitate TPLO plate placement parallel to the tibial long-axis and TPLO screw placement parallel to the joint surface. By providing multiple plates with different offsets, the surgeon is allowed to choose the preferred tibial plateau (tuberosity) translation or adapt to variable anatomy.

BRIEF DESCRIPTION OF THE DRAWINGS

The foregoing features will be apparent from the following Detailed Description, taken in connection with the accompanying drawings, in which.

DETAILED DESCRIPTION

The present disclosure relates to a tibial plateau leveling osteotomy (TPLO) plate with offset for a tibial plateau leveling osteotomy. The offset allows for translation of the osteotomized segment medially or laterally for alignment of the tibia, patella and quadriceps. This plate can be used for an apparatus in veterinary surgery for orthopedic surgical translation of an osteotomized segment in canines, felines, and other quadruped animal species, both domestic and exotic. The plate can be used to repair a torn cranial cruciate ligament while concurrently repairing a chronic pre-existing patella luxation.

The TPLO plate with offset allows translation of a proximal tibial segment while maintaining plate alignment parallel to a tibial long axis and screw alignment parallel a joint surface to minimize the risk of unacceptable screw impingement. The TPLO with offset minimizes plate-to-bone distance to minimize a risk of screw failure, and allows a surgeon to adapt to abnormal anatomy while maintaining a plate parallel to the tibial long axis to reduce risk of complications.

The present disclosure relates to a tibial plateau leveling osteotomy (TPLO) plate with an offset. The TPLO plate with offset includes distal portion, an offset portion, and a proximate portion. The distal portion includes attachment apertures to secure the TPLO plate with offset to the body of the tibia. The proximal portion includes attachment apertures to secure the TPLO plate to an upper portion of a tibia or the osteotomized section of a tibia. The offset portion connects the proximal portion and the distal portion in an offset relation. The offset portion can be at 90° with respect to both the distal portion and the proximal portion such that the distal portion and the proximal portion are in parallel planes offset from each other. The length of the offset portion can be varied.

Figure 1:
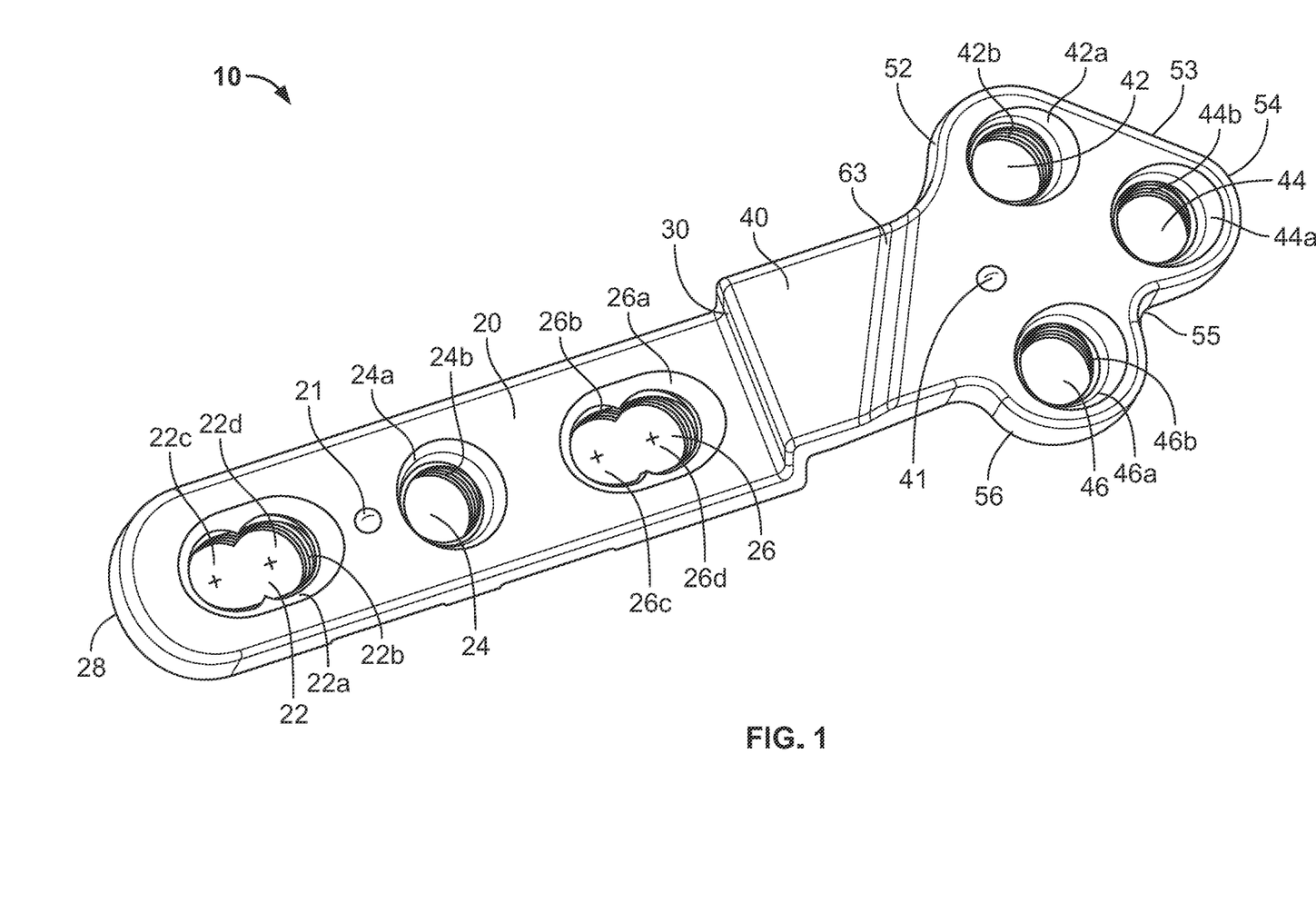
FIG. 1 is a perspective view of a tibial plateau leveling osteotomy plate with offset apparatus.
Figure 2:
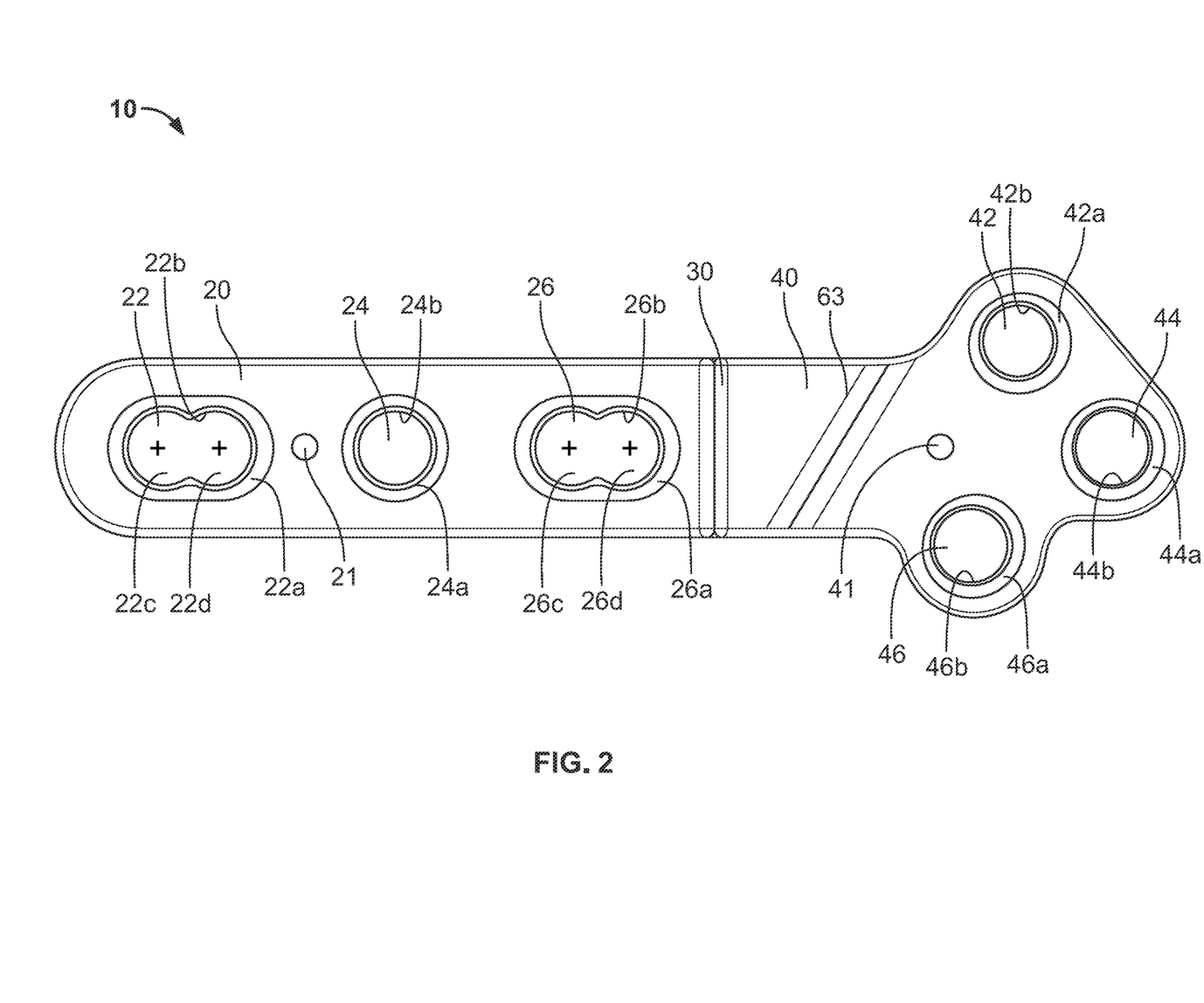
FIG. 2 is a top view of the apparatus shown in FIG. 1.
Figure 3:
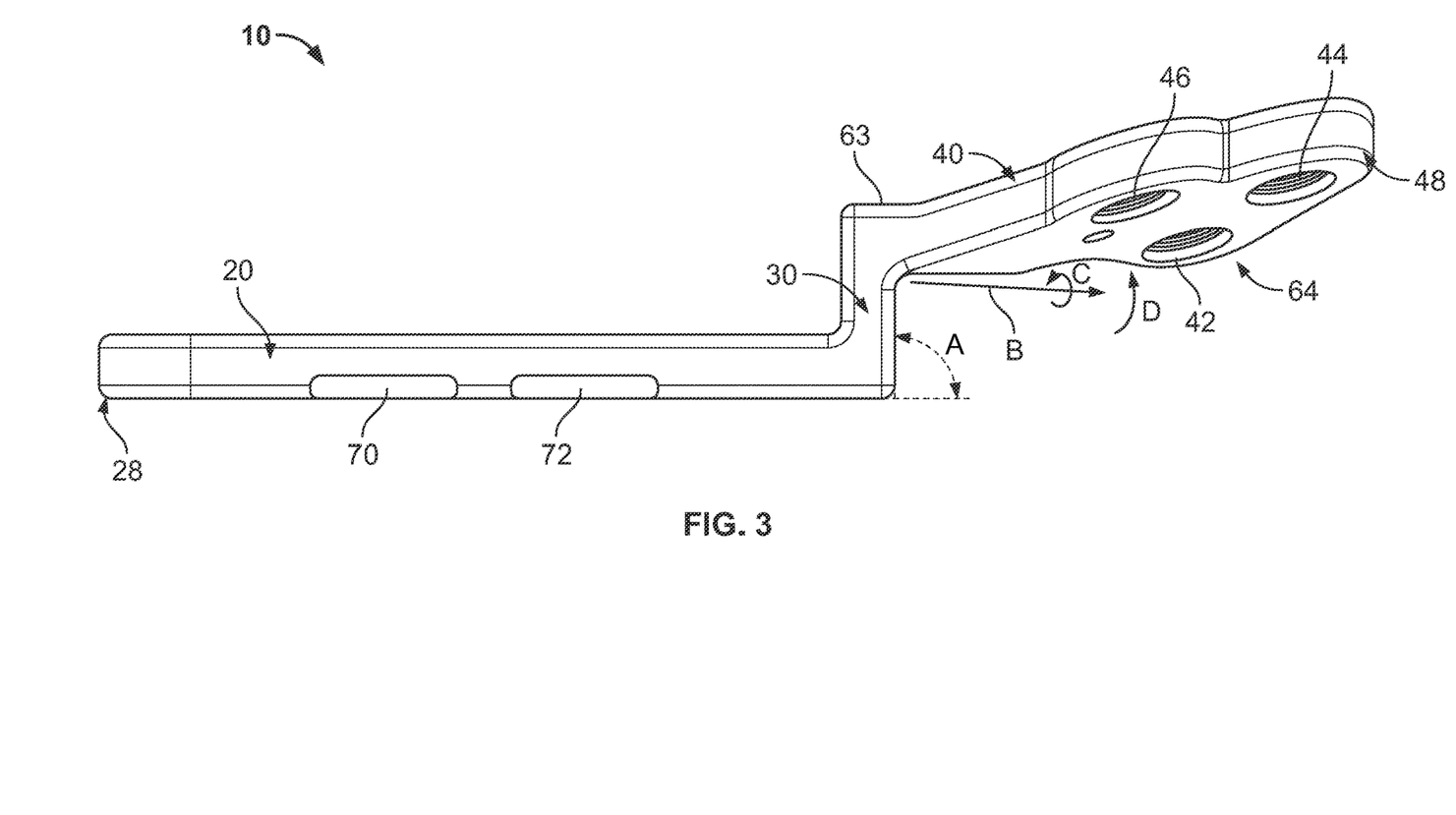
FIG. 3 is a side view of the apparatus shown in FIG. 1.

Referring now to the drawings in detail wherein like numerals refer to like elements throughout the several views, one see that FIGS. 1-3 show the TPLO plate with offset, indicated generally at 10. Specifically, FIG. 1 shows a perspective view, FIG. 2 shows a top view, and FIG. 3 shows a side view of the TPLO plate 10 with offset. The TPLO plate with offset 10 comprises three portions: a distal portion 20, an offset portion 30, and a proximal portion 40.

The distal portion 20 includes one or more dual attachment apertures such as the illustrated dual-attachment apertures 22, 26. A one single attachment aperture 24 can also be included to secure the plate 10 to the body of the tibia. Apertures 22, 24, 26 include respective chamfered entrances 22a, 24a, 26a to capture an attachment device (see elements 200, FIGS. 4 and 6), and can have threaded portions 22b, 24b, and 26b for locking/threaded fixation hardware. Furthermore, dual attachment apertures 22, 26 are formed with two axes of rotation, offset from one another, 22c, 22d and 24c, 24d, respectively, each axis of which can have threaded portions. A pilot aperture 21, illustrated as configured as a hemispherical blind aperture, can be used for preliminary attachment. Any suitable type of attachment aperture can be used such as a single position aperture 24 or multiple position apertures 22 and 26. The apertures can be locking, as shown, with threading at lower portions thereof, or non-locking. The apertures can also be compression apertures. The attachment apertures 22, 24, 26 can be positioned linearly along a center or longitudinal axis of the distal portion 20 for proper attachment to a bone. However, the attachment apertures 22, 24, 26 can also be offset from the center axis of the distal portion 20 if desired. An end 28 of the distal portion 20 can be contoured to be elevated away from the bone of the distal tibia so as not to impede tibial soft tissues. For example, a clearance of 1-2 mm may be provided.

The proximal portion 40 includes attachment apertures 42, 44, 46, formed along the edge of proximal portion in a semi-circular configuration, which are used to secure the proximal portion 40 of the plate 10 to an upper portion of a bone, such as an osteotomized section of a tibia. Similar to attachment apertures 22, 24, 26, attachment apertures 42, 44, 46 include respective chamfered entrances 42a, 44a, 46a to capture an attachment device (see elements 200, FIGS. 4 and 6), and can have threaded portions 42b, 44b, and 46b for locking/threaded fixation hardware. A pilot aperture 41, illustrated as configured as a hemispherical blind aperture, can be used for preliminary attachment.

The proximal portion 40 can take on any suitable shape, such as linear, triangular, etc. As shown in the Figures, the proximal portion 40 could have a general triangular shape with first and second bulges 52 and 56 corresponding to attachment apertures 42 and 46, a generally straight edge 53, leading to a curved edge 54, around attachment aperture 44, and an edge 55 with a scalloped indentation between attachment apertures 44 and 46.

The attachment apertures 42, 44, 46 can be positioned in any location on the proximal portion 40 for proper attachment to an osteotomized segment of a bone. For example, attachment aperture 44 can be positioned at the apex of the plate 10 with its center being at a center plane running the length of the plate 10, attachment aperture 42 can be positioned towards the offset portion, flanking attachment aperture 44. An end 48 of the proximal portion 40 can be contoured to be elevated away from the bone of the distal tibia so as not to impede tibial soft tissues. For example, a clearance of 1-2 mm can be provided. Each attachment aperture 42, 44, 46 can comprise a fully or partially rounded exterior surface. It should be understood that the proximal portion 40 can contain any number of attachment apertures, such as two or more.

Each of the attachment apertures 22, 24, 26, 42, 44, 46 can be designed to receive a fastener, such as a bolt, a screw, or any other applicable fastening device (see element 200, FIGS. 4 and 6) Accordingly, these apertures can be threaded, tapered, rounded, etc. In the case of the dual attachment apertures 22, 26, these apertures can have multiple locations (e.g., apertures) for receiving a fastener, such as a screw. Each of the attachment apertures 22, 24, 26, 42, 44, 46 can be aligned and extend through the front and back of generally planar faces. The diameter of the attachment apertures 22, 24, 26, 42, 44, 46 (including each dual aperture within attachment apertures 22, 26) can vary such that they can accept appropriate sized screw, or other fastener. For example, the attachment apertures 22, 24, 26, 42, 44, 46 could be 3.5 mm in diameter, to allow for the placement of a 3.5 mm cortical bone screw. These apertures can be sized to have a sufficient diameter such that the head of the screw, such as a 3.5 mm cortical screw, fits flush with the distal and proximal portions 20 and 40. Other sized bone screws, such as 2.0 mm, 2.7 mm, or 3.5 mm cortical bone screws can also be used, and the apertures could be sized accordingly to the given application.

As shown in the Figures, the apertures 22, 24, 26, 42, 44, 46 can have a round or oblong profile to act as compression type holes. The overlapping holes include angled surfaces that create a compression effect as the TPLO plate 10 is attached to the bone 100, such that while the plate 10 is connected to a bone 100 via screws 200 mounted through the apertures a compressive force is imparted to the bone sections which causes the bone sections to move towards the center of the plate 10.

The apertures 22, 24, 26, 42, 44, 46 are shown with locking screw holes are threaded and designed to work with different designs of locking screws 200. Locking screws 200 thread into the plate 10 as well as into the bone 100.

The offset portion 30 links the distal portion 20 and the proximal portion 40 such that the proximal portion 40 is situated on a plane offset from the distal portion 20 but generally parallel thereto. The offset portion 30 can be oriented at angle A of 90° with respect to the distal and proximal portions 20 and 40, and this angle can be varied if desired. Accordingly, there is a first angle between the distal portion 20 and the offset portion 30, and a second angle between the offset portion 30 and the proximal portion 40. The offset portion 30 is generally perpendicular to the distal and proximal portions 20 and 40. The angle of the offset portion 30 could be less than perpendicular to facilitate manufacturing by stamping. The length of the offset portion 30 can be varied as suitable to the given application.

Different offsets can be used for different sized implants intended for various sized animals, and can be scaled in accordance to the average needs of a patient group. For example, a 3.5 mm plate can be designed with different offsets to allow for a range of accommodations. Any amount of offset could be engineered into the TPLO plate 10, such as a range of, for example, between 3 mm and 10 mm or more or less. Additionally, the proximal portion 40 may optionally include a bend 63 thereby causing an angle or curvature 64 (see FIG. 3), where the proximal portion 40 has a twist or a bend 63 to better attach to a osteotomized section of bone and further causing a portion of the proximal portion 40 to be on a plane which is twisted, rotated or inclined with respect to the plane of the remaining portion of the proximal portion 40. This twist, rotation or inclination is illustrated by a rotation C about axis B, or an inclination of axis B as indicated by arrow D in FIG. 3. As such, the proximal portion can be angled or turned about a long axis of the plate 10 so that a contact face of the proximal portion 40 is at an angle with respect to a contact face of the distal portion 20. Typically, however, the portion of proximal portion 40 immediately adjacent to offset portion 30 is in a plane parallel with that of distal portion 20. Other embodiments may include a proximal portion 40 which is entirely in a plane parallel to that of distal portion 20.

As further illustrated in FIG. 3, the lower surface of distal portion 20 can include undercuts 70, 72 (some embodiments includes similar undercuts on the opposite unillustrated side of distal portion 20).

The TPLO plate 10 with offset can be formed from any number of biocompatible, implantable materials. These materials include, but are not limited to, 316 stainless steel, titanium, or ultra-high-molecular-weight polyethylene. Exposed edges of the plate 10 can be rounded and smooth. The length of the plate 10 can vary with the size of the patient. Similarly, the thickness of the plate 10 can vary with the size of the patient.

Figure 4:
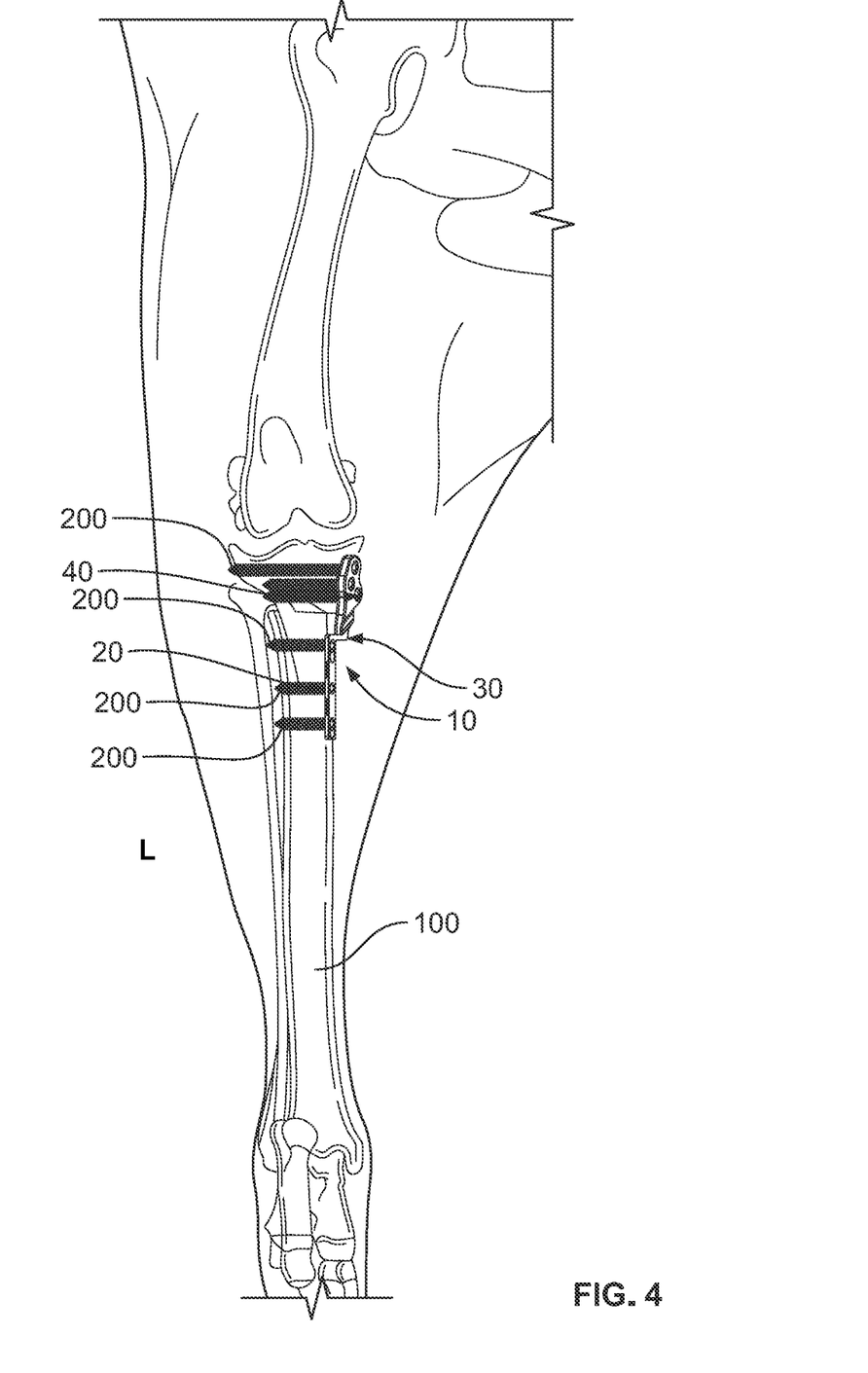
FIG. 4 illustrates a side view of the apparatus of FIG. 1 implanted in a canine's leg.
Figure 5:
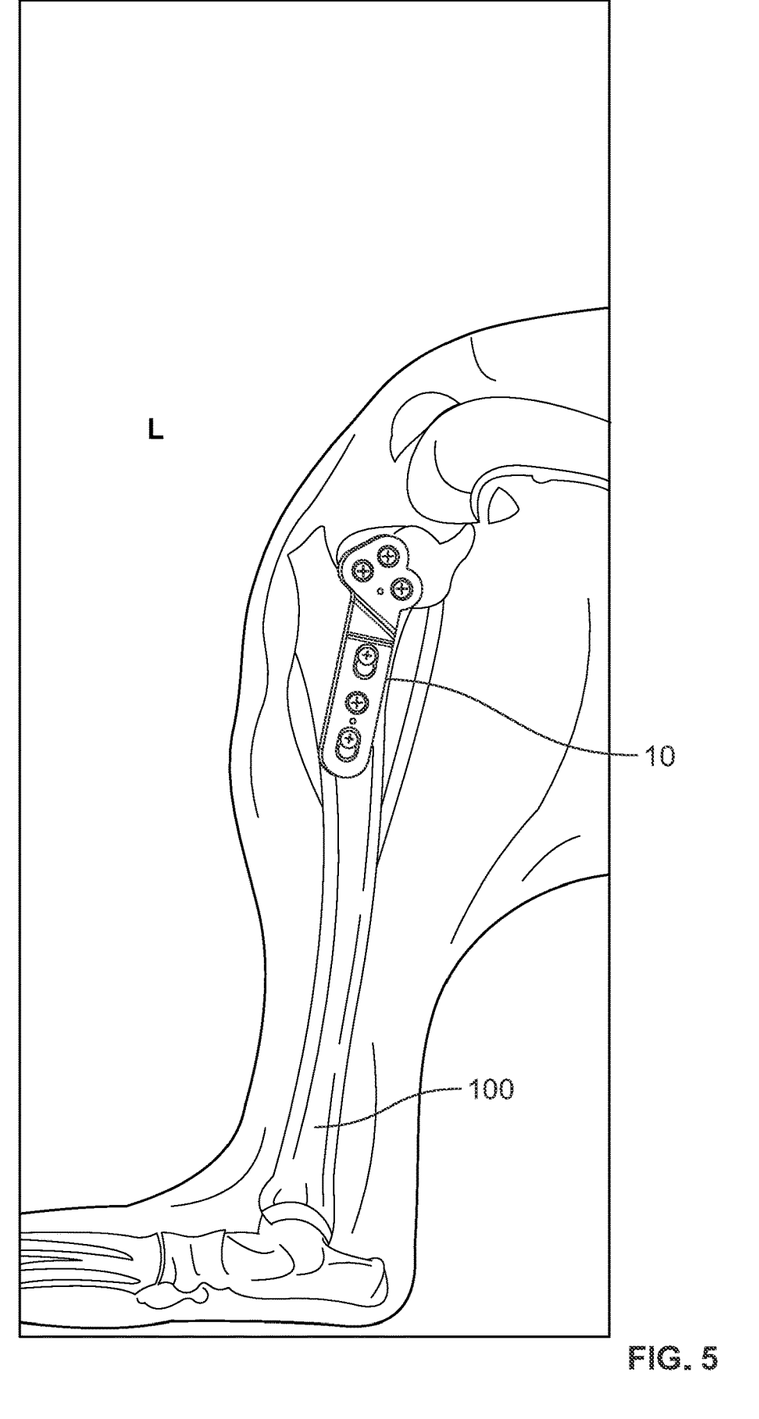
FIG. 5 illustrates a top view of the apparatus of FIG. 1 implanted in the canine's leg.
Figure 6:
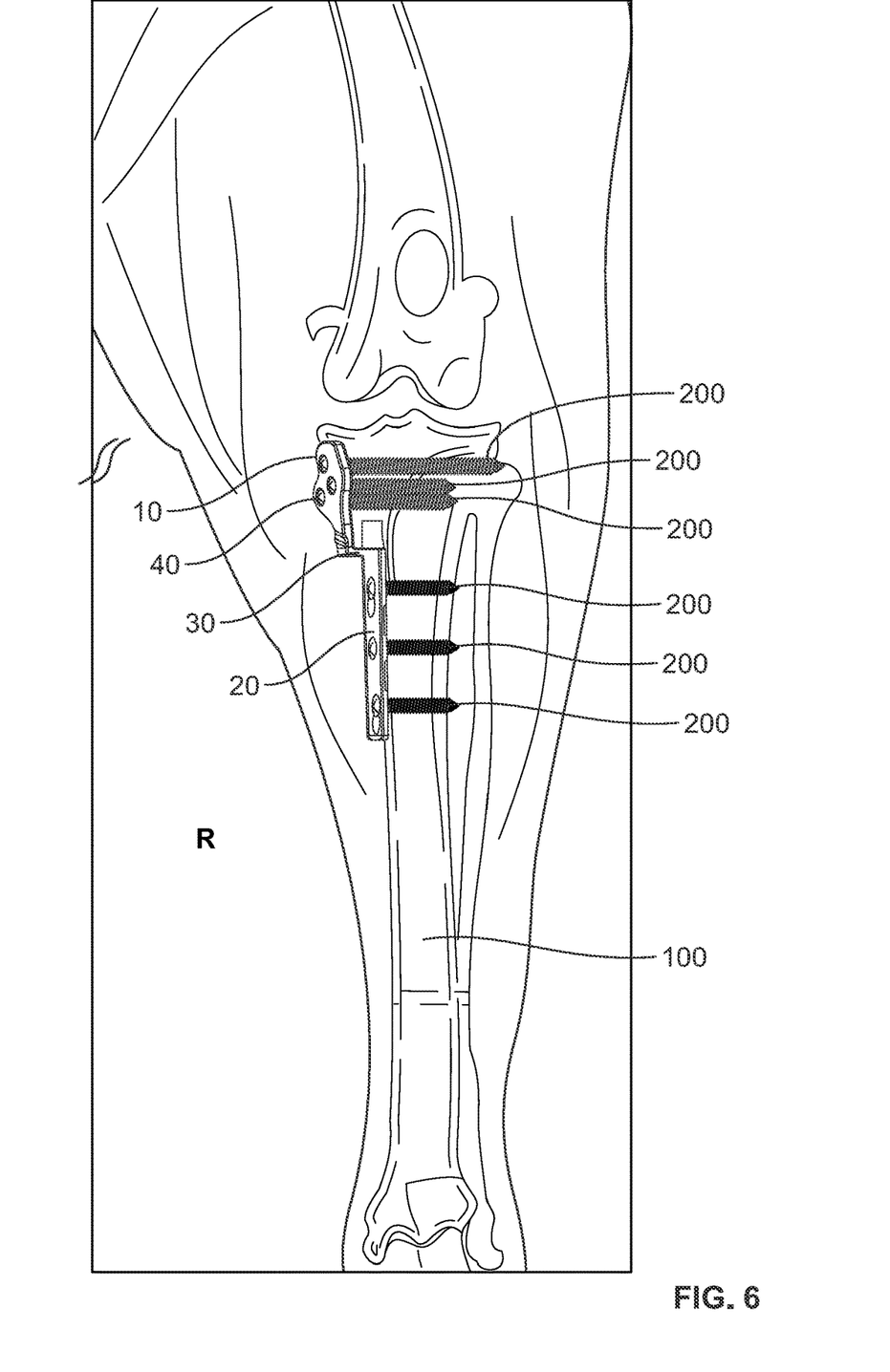
FIG. 6 illustrates a further side view of the apparatus of FIG. 1 implanted in a canine's leg.

FIGS. 4, 5 and 6 illustrate the TPLO plate with offset 10 affixed to a canine's leg bone 100 and attached by attachment elements 200. Specifically, FIGS. 4 and 6 illustrate a side view of the TPLO plate 10 with offset affixed to the canine's leg. The distal end 20 of the plate 10 is secured to the body of the canine's tibia. The proximal end 40 of the plate 10 is secured to an osteotomized section of the canine's tibia. FIG. 5 illustrates a top view of the TPLO plate with offset 10 affixed to the canine's leg.

Having thus described the system and method in detail, it is to be understood that the foregoing description is not intended to limit the spirit or scope thereof. It will be understood that the embodiments of the present disclosure described herein are merely exemplary and that a person skilled in the art can make any variations and modification without departing from the spirit and scope of the disclosure. All such variations and modifications, including those discussed above, are intended to be included within the scope of the disclosure.

What is claimed is:

1. A tibial plateau leveling osteotomy plate, including:
   a proximal portion including at least one first attachment aperture, wherein the proximal portion comprises a first portion and a second portion, wherein the first portion is distal of the second portion;
   a distal portion including at least one second attachment aperture; and
   an offset portion extending substantially perpendicularly from the distal portion to the first portion of the proximal portion thereby joining the proximal portion to the distal portion, wherein the distal portion is on a first plane, and wherein the first portion of the proximal portion is on a second plane different from the first plane of the distal portion;
   wherein the second plane of the first portion of the proximal portion is substantially parallel to the first plane of the distal portion; and
   wherein the second portion of the proximal portion is on a third plane and is inclined upwardly relative to the second plane of the first portion of the proximal portion and extends away from the first plane of the distal portion.

2. The plate of claim 1 wherein the second portion of the proximal portion is twisted with respect to the second plane of the first portion of the proximal portion.

3. The plate of claim 2 wherein the second portion is twisted around a longitudinal axis of the plate relative to the second plane.

4. The plate of claim 1 wherein the second portion of the proximal portion is rotated with respect to the second plane of the first portion of the proximal portion.

5. The plate of claim 4 wherein the second portion is rotated around a longitudinal axis of the plate relative to the second plane.

6. The plate of claim 1 wherein the at least one first attachment aperture is on the second portion of the proximal portion.

7. The plate of claim 6 wherein the at least one first attachment aperture includes a plurality of first attachment apertures arranged in a generally triangular configuration.

8. The plate of claim 7 wherein the at least one second attachment aperture includes a plurality of second attachment apertures.

9. The plate of claim 8 wherein at least a portion of the plurality of second attachment apertures include dual attachment apertures with two axes of rotation offset from each other.

10. The plate of claim 1 wherein the plate is sized and shaped for veterinary surgical applications.

11. The plate of claim 10 wherein the plate is adapted for surgical applications with canines, felines or quadruped animals.

12. The plate of claim 1 wherein the plate is made from a material chosen from the group consisting of 316 stainless steel, titanium, and ultra-high-molecular-weight polyethylene.

13. The plate of claim 1 wherein the offset portion comprises a first wall facing toward the distal portion and a second wall facing toward the proximal portion, wherein the first wall is parallel to the second wall.

14. The plate of claim 1 wherein the plate further comprises a bend between the first portion of the proximal portion and the second portion of the proximal portion, and from a top view the bend and the offset portion form an angle.

15. The plate of claim 1 wherein the second portion of the proximal portion extends away from the first plane of the distal portion in a distal to proximal direction.

16. A tibial plateau leveling osteotomy plate, including:
    a proximal portion including at least one first attachment aperture, the proximal portion comprising a first portion and a second portion, wherein the first portion is distal of the second portion;
    a distal portion including at least one second attachment aperture; and
    an offset portion extending substantially perpendicular to, and attached to, both the proximal portion and the distal portion, wherein the distal portion is in a first plane and the first portion of the proximal portion is in a second plane different from and substantially parallel to the first plane;
    wherein the second portion of the proximal portion is in a third plane which is rotated around the longitudinal axis of the plate relative to the second plane of the first portion of the proximal portion; and
    wherein the plate further comprises a bend between the first portion of the proximal portion and the second portion of the proximal portion, wherein the bend forms an angle between the third plane and the longitudinal axis such that the third plane is inclined relative to and intersects with the longitudinal axis.

17. The plate of claim 16 wherein the at least one first attachment aperture includes a plurality of first attachment apertures.

18. The plate of claim 17 wherein a first one of the plurality of first attachment apertures on the proximal portion is arranged in line with the second attachment apertures on the distal portion.

19. The plate of claim 18 wherein the first one of the first attachment apertures is flanked on either side by second and third ones of the first attachment apertures on the proximal portion.

20. The plate of claim 16 wherein the first portion of the proximal portion is distal of the second portion, and the offset portion is attached to the first portion of the proximal portion.

21. The plate of claim 16 wherein a contact face of the second portion of the proximal portion is disposed at an angle relative to a contact face of the distal portion.

* * * * *